(12) United States Patent
Armand et al.

(10) Patent No.: US 8,927,160 B2
(45) Date of Patent: Jan. 6, 2015

(54) PENTACYCLIC ANION SALT AND USE THEREOF AS AN ELECTROLYTE

(75) Inventors: Michel Armand, Paris (FR); Sylvie Grugeon, Feuquieres (FR); Stephane Laruelle, Saveuse (FR); Maria Bukowska, Varsovie (PL); Przemyslaw Szczecinski, Varsovie (PL); Wladyslaw Wieczorek, Mysiadlo (PL); Leszek Niedzicky, Varsovie (PL); Bruno Scrosati, Rome (IT); Stefania Panero, Rome (IT); Priscilla Realle, Latina (IT)

(73) Assignees: Centre National de la Recherche Scientifique, Paris (FR); Universite de Rome "La Sapienza", Rome (IT); Universite de Picardie Jules Verne, Amiens (FR); Universite de Technologie de Varsovie, Varsovie (PL)

( * ) Notice: Subject to any disclaimer, the term of this patent is extended or adjusted under 35 U.S.C. 154(b) by 902 days.

(21) Appl. No.: 13/060,776

(22) PCT Filed: Aug. 28, 2009

(86) PCT No.: PCT/FR2009/051642
§ 371 (c)(1),
(2), (4) Date: Sep. 7, 2011

(87) PCT Pub. No.: WO2010/023413
PCT Pub. Date: Mar. 4, 2010

(65) Prior Publication Data
US 2011/0311884 A1    Dec. 22, 2011

(30) Foreign Application Priority Data
Aug. 29, 2008    (FR) ..................... 08 04769

(51) Int. Cl.
| | |
|---|---|
| *H01M 6/16* | (2006.01) |
| *H01M 10/0568* | (2010.01) |
| *B22F 9/24* | (2006.01) |
| *C07D 233/00* | (2006.01) |
| *C22B 5/00* | (2006.01) |
| *H01M 4/58* | (2010.01) |
| *H01M 10/0525* | (2010.01) |

(52) U.S. Cl.
CPC ............. *H01M 10/0568* (2013.01); *B22F 9/24* (2013.01); *C07D 233/00* (2013.01); *C22B 5/00* (2013.01); *B22F 2009/245* (2013.01); *B22F 2999/00* (2013.01); *H01M 4/5825* (2013.01); *H01M 10/0525* (2013.01)
USPC ........................................ 429/333

(58) Field of Classification Search
None
See application file for complete search history.

(56) References Cited

U.S. PATENT DOCUMENTS

| | | | |
|---|---|---|---|
| 3,793,339 | A | 2/1974 | Webster |
| 6,395,367 | B1 * | 5/2002 | Michot et al. ................ 428/64.8 |
| 6,835,495 | B2 * | 12/2004 | Michot et al. ................ 429/188 |
| 2005/0123831 | A1 * | 6/2005 | Michot et al. ................ 429/188 |
| 2007/0219379 | A1 * | 9/2007 | Itoh et al. ................... 548/343.1 |

FOREIGN PATENT DOCUMENTS

| | | |
|---|---|---|
| DE | 10 2006 013871 | 9/2007 |
| EP | 0 850 933 | 7/1998 |

OTHER PUBLICATIONS

Search Report dated Aug. 28, 2009.
Modern generation of polymer electrolytes based on lithium conductive imidazole salts.
Platinum nanoparticles prepared by a plasma-chemical reduction method.
Hydrogen Cyanide Chemistry VIII New Chemistry of Diaminomaleonitrile Heterocyclic Synthesis.

* cited by examiner

*Primary Examiner* — Patrick Ryan
*Assistant Examiner* — Lucas J O Donnell
(74) *Attorney, Agent, or Firm* — Sofer & Haroun, LLP

(57) ABSTRACT

The invention relates to a pentacyclic anion salt and to the use thereof in electrolyte compositions. The compound comprises an inorganic, organic or organometallic cation M of valency m (1≤m≤3) and m anions corresponding to the formula (I) in which $R_f$ is a —CFZ'Z" group in which Z' is F or a perfluoroalkyl group having from 1 to 3 carbon atoms, and Z" is an H, F or Cl group, an optionally fluorinated or perfluorinated alkoxy group having from 1 to 5 carbon atoms, an optionally fluorinated or perfluorinated oxaalkoxy group having from 1 to 5 carbon atoms or an optionally fluorinated or perfluorinated alkyl group having from 1 to 5 carbon atoms; Z" being other than F when Z' is F. An electrolyte composition comprises said salt in solution in a liquid solvent or a polymer solvent.

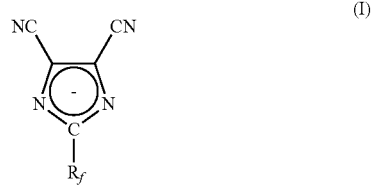

9 Claims, 2 Drawing Sheets

PENTACYCLIC ANION SALT AND USE THEREOF AS AN ELECTROLYTE

RELATED APPLICATIONS

This application is a National Phase application of PCT/FR2009/051642, filed on Aug. 28, 2009, which in turn claims the benefit of priority from French Patent Application No. 08 04769, filed on Aug. 29, 2008, the entirety of which are incorporated herein by reference

BACKGROUND

1. Field of the Invention

The present invention relates to ionic compounds of use in the preparation of an electrolyte for batteries.

2. Description of Related Art

Electrolyte solutions in a nonaqueous medium, in particular a nonprotogenic medium, more commonly referred to as an "aprotic" medium, are of great technological importance as they make it possible to extend the potential range in which a battery can operate without side reactions, such as the decomposition of the solvent, said potential not exceeding the value of 1.3 V in water.

The media capable of dissolving salts are mainly polar organic solvents or solvating polymers, in particular those comprising ether groups distributed in a macromolecular chain, the architecture of which can be linear or branched, of comb type, having or not having crosslinking nodes. The polyethers having —$CH_2CH_2O$— repeat units are particularly valued for their high solvating power.

Ionic liquids are also known, which products are salts which are molten at low temperature and which are composed of at least one cation possessing a delocalized charge, such as (ethyl)(methyl)imidazolium (EMI), (methyl)(propyl)-pyrrolidinium or diethylmethyl(2-methoxyethyl)ammonium, and of an anion, preferably itself also possessing a charge delocalized over a large volume, in order to reduce the interactions between the cations and the anions and to thus make it possible to achieve low solidifying temperatures.

The solutes intended to introduce the conductivity of ionic type required for the electrolytes are chosen from metal salts and from "ium" salts obtained by binding of a free electron pair of one or more elements, such as N, O, S, P, As or I, with a proton or an organic radical, to form a cation. Mention may be made of ammonium, phosphonium, sulfonium, iodonium, pyridinium, imidazolium, oxazolium and thiazolium ions. Particular importance is given, among metals, to alkali metal and alkaline earth metal salts, in particular to lithium salts. The lithium ion in fact has a very rich electrochemistry, making it possible to form batteries having a high energy density which are very important in current technology. Mention may be made, as other applications of nonaqueous electrolytes, of electrochromic systems and supercapacitors.

The anions which act as countercharge to the cations are chosen from those which exhibit a delocalized negative charge as aprotic electrolytes cannot form hydrogen atoms with negative charges and delocalization is the only means of obtaining appreciable dissociation under these conditions. Mention may be made, among the most well-known anions, of $ClO_4^-$, $BF_4^-$, $PF_6^-$, $AsF_6^-$ or $SbF_6^-$. The $ClO_4^-$ anion can form explosive mixtures. The anions derived from As and Sb are toxic and uncommon. The $BF_4^-$ anion is relatively slightly dissociated. The salts of the $LiPF_6$ anion are the most widely used salts in lithium generators, despite major disadvantages: i) they are very readily hydrolyzable, releasing HF, which is toxic and corrosive with regard to the electrode materials. HF releases cations (Mn, Fe, and the like) from the positive electrode and allows them to migrate to the negative electrode, where they are reduced ($Mn°$, $Fe°$, and the like), which significantly increases the interfacial impedance of this electrode, reducing the power available and the lifetime; ii) the acid/base equilibrium $LiPF_6 \Leftrightarrow LiF+PF_5$ releases a very powerful Lewis acid capable of inducing carbocationic chemistry destructive in particular to esters or ethers from which the electrolytic solvent may be formed; iii) in the event of an uncontrolled reaction ("runaway reaction") with strong heating, $LiPF_6$ can act as fluorinating agent, giving monofluoroethanol or monofluoroacetic acid derivatives, which are excessively toxic.

A fluorine-free coordination anion is also known, in particular bis(oxalato)borate $[B(C_2O_4)_2]^-$, which employs inexpensive elements; however, its lithium salt has a limited conductivity. The rigidity of the anion and its large size give it an unfavorable phase diagram in standard electrolytes comprising ethylene carbonate (poor conductivity at low temperature). Furthermore, this anion has a very limited stability toward oxidation at high temperature (65° C.), which causes problems of self-discharge and of release of gas.

Other anions are known which exhibit high electrochemical stability and high conductivities, both in liquids and in polymers. Among these, the anions capable of forming an anionic liquid are the most effective. The main family is that of the sulfonimides $[(R_FSO_2)_2N]^-$, the most important representative of which corresponds to $R_F$=$CF_3$ (TFSI). The disadvantages of these salts are due, on the one hand, to the absence of passivation of the aluminum above 3.6 V vs. $Li^+:Li°$ when the salts are used in batteries or supercapacitors which have an electrode having a current collector made of aluminum. Another disadvantage is the high preparation cost, related to the price of the $CF_3SO_2$ synthon. The $[(FSO_2)_2N]^-$ anion would have a more favorable behavior with regard to the corrosion of the aluminum but it is very expensive to prepare and the stability of the lithium salt is limited (130° C.). Generally, it appears that the corrosion of the aluminum is inevitable above 3.6 volts when the electrolyte comprises a salt of a covalent anion as a soluble aluminum salt (such as, for example, the TFSI salt $[(CF_3SO_2)_2N]_3Al$, which is stable and very soluble) can be formed which does not make it possible to passivate the surface of the metal. On the other hand, a coordination anion, such as $PF_6^-$, does not form $(PF_6)_3Al$ but the $AlF_3$ salt, which is insoluble and passivating.

Other anions, "Hückel anions", are based on the adaptation of the Hückel (4n+2) rule, which predicts the stability of aromatic systems, applied to rings comprising five atoms, the negative charge of which is highly favored. The best known of these anions is 4,5-dicyanotriazole (DCTA):

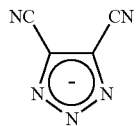

This purely covalent anion can be regarded as having a 6 "π" electron configuration or a 10 "π" electron configuration, according to whether or not the electrons of the C≡N bonds of the nitrile groups are taken into account, each of these configurations being stable. DCTA salts are thermally stable up to 300° C. Furthermore, the DCTA anion does not comprise fluorine and it is easily manufactured from an industrial precursor, diaminomaleonitrile (DAMN):

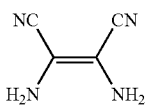

However, this anion has the disadvantage of a relatively modest conductivity of its lithium salt (2.9 mS·cm$^{-1}$ in EC-DMC 50/50) and in particular an oxidation potential of 3.7 V vs. Li$^+$:Li$^\circ$, which limits its use in a totally unacceptable way for electrode materials such as transition metal oxides Li$_x$T$^M$O$_2$ (0≤x≤1) with T$^M$=Mn, Ni or Co, the manganese phosphate LiMnPO$_4$ or its solid solutions with the iron phosphate LiMn$_{1-y}$Fe$_y$PO$_4$ (0≤y<1). Even for the iron phosphate (y=1) having a potential of 3.5 V vs. Li$^+$:Li$^\circ$, the safety margin at the end of charging the electrode is too small.

Salts of anions corresponding to the formula:

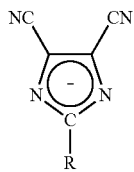

in which R is an electron-withdrawing group, for example a perfluoroalkylsulfonyl group or a perfluoroalkylcarbonyl group, are known, in particular from EP-0 850 933-A. However, despite the high attractive power of the R group, the presence of oxygen (C═O and O═S═O), which gives very strong interactions with the cations, limits the dissociation. In addition, the C═O or S═O groups are conjugated with the ring and the number of "π" (electrons is a multiple of 4. The result of this is that the systems are "antiaromatic" and that they thus have a lower stability toward oxidation and toward reduction. Furthermore, the preparation of in this type of compound is very difficult and cannot be carried out in a single stage starting from DAMN.

The synthesis of 2-trifluoromethyl-4,5-dicyanoimidazole is described by M. Bukowska et al. [Polish J. Chem., 78, 417-422 (2004)]. The corresponding lithium salt can be obtained by reaction with lithium carbonate.

OBJECTS AND SUMMARY

The aim of the present invention is to provide salts which can be used as electrolyte in lithium electrochemical devices, said salts being stable at high temperatures and at potentials of greater than 4 V vs. Li$^+$:Li$^\circ$.

A compound (1) according to the present invention has a cation M of valency in (1≤m≤3) and m anions corresponding to the formula:

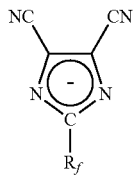

in which R$_f$ is a —CFZ'Z" group in which:
  Z' is F or a perfluoroalkyl group having from 1 to 3 carbon atoms, Z" is an H, F or Cl group, an optionally fluorinated or perfluorinated alkoxy group having from 1 to 5 carbon atoms, an optionally fluorinated or perfluorinated oxaalcoxy group having from 1 to 5 carbon atoms or an optionally fluorinated or perfluorinated alkyl group having from 1 to 5 carbon atoms; Z" being other than F when M is Li and Z' is F.

Mention may be made, as examples, of the following R$_f$ groups: CF$_2$H, CF$_2$Cl, C$_2$F$_5$, CF$_2$CF$_2$H, C$_3$F$_7$, C$_4$F$_9$, CF$_2$OCH$_3$, CF$_2$OC$_2$H$_5$, CF$_2$OC$_2$H$_4$OCH$_3$, CF$_2$OC$_2$H$_4$OC$_2$H$_5$, CF$_2$OCH$_2$OCF$_3$, CF(CF$_3$)OCH$_3$, CF(CF$_3$)OC$_2$H$_5$, CF(CF$_3$)OC$_2$H$_4$OCH$_3$, CF(CF$_3$)OC$_2$H$_4$OC$_2$H$_5$ and CF(CF$_3$)OCH$_2$CF$_3$.

The cations are chosen from inorganic cations, organometallic cations and organic cations.

An inorganic cation can be chosen from alkali metal cations, alkaline earth metal cations and the ammonium ion. Preference is given in particular to the Li$^+$, Na$^+$, NH$_4^+$, Ca$^{++}$ and Ba$^{++}$ ions.

An organometallic cation can be chosen from ferricinium, titanocenium and zirconocenium ions. Mention may in particular be made of the ferricinium cation [C$_5$H$_5$)$_2$Fe]$^+$, the titanocenium cation [C$_5$H$_5$)$_2$Ti]$^{2+}$ and the zirconocenium cation [C$_5$H$_5$)$_2$Zr]$^{2+}$.

An organic cation can be chosen from ammonium, phosphonium, sulfonium, iodonium, pyridinium, imidazolium, pyrazolium, acetamidium, oxazolium, thiazolium, pyrrolidinium and piperidinium ions. Mention may be in particular be made of cations which correspond to the following formulae, in which:

R$^1$ to R$^{37}$ each represent H or an alkyl, aryl or oxaalkyl group of 1 to 20 carbon atoms;

R$^5$ to R$^{13}$ each represent an aryl group, an alkylaryl group or a dialkylamino group R$^{37}$R$^{38}$N in which the R$^{37}$ and R$^{38}$ groups are alkyl groups having from 1 to 20 carbon atoms;

or else two R groups carried by adjacent carbon atoms together form a diradical forming an aliphatic or aromatic ring.

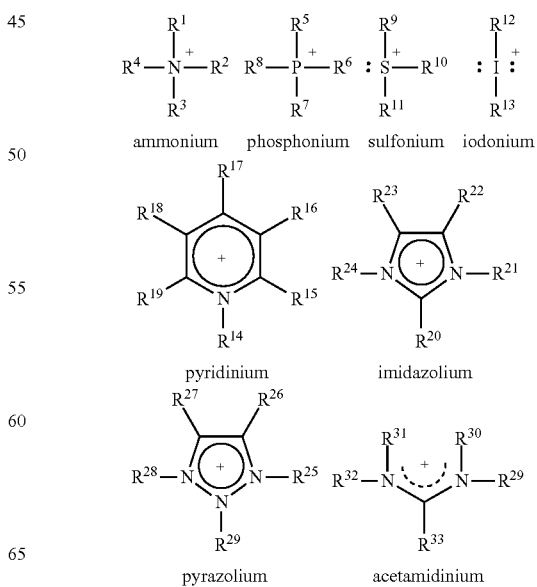

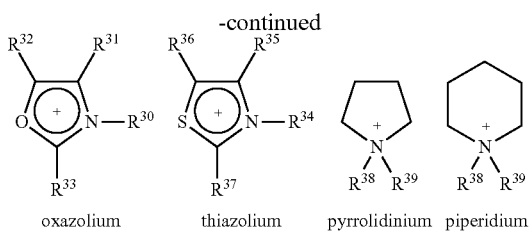

oxazolium    thiazolium    pyrrolidinium    piperidium

The pyrrolidinium and piperidium ions are two important examples of quaternary ammonium in which two substituents of the nitrogen together form a ring.

In a specific embodiment, the ionic compound of the invention comprises an organic polycationic part in association with the number of anions required to provide the electroneutrality of the compound. The polycationic part comprises at least two repeat units which each carry a cationic group. According to an alternative form, the repeat unit of the polycationic part can be a unit carrying a cationic side group, for example one of the above cations in which one of the R groups is a diradical for bonding with a repeat unit forming the chain of the polycationic group. According to another alternative form, the cationic groups form part of the chain of the polycationic group, two R substituents on a cationic group being diradicals which form a bond with adjacent cationic groups.

An ionic compound of the invention in which the cation is an organic or organometallic cation is of use in electrochromic systems in which it can act as counterelectrode, in particular the ferrocene/ferricinium system of low absorbency. Such a compound can also be used in electrochemical actuators which convert an electrical signal into mechanical movement, in particular the actuators comprising conjugated polymers of polythiophene or polyaniline type, the doping/dedoping of which with bulky cations brings about mechanical movements which can be controlled by the applied current.

An ionic compound of the invention in which the cation is an organic or organometallic cation and which is liquid at a temperature of less than 100° C. forms an ionic liquid which can be used as solvent for alkali metal salts, in particular in electrochemical generators. Such a compound is particularly advantageous in this use owing to the fact that it is nonflammable.

An ionic compound of the invention in which the cation is an cationic or organometallic cation can also be used to carry out electrochemical depositions of metals, such as aluminum, tantalum, niobium, tin, copper, chromium, platinum, palladium and zinc. These metals are important as protection against corrosion or as catalysts, in particular in the form of nanoparticles. The nanoparticles of a metal are particularly easy to obtain by dissolution of a salt of the metal in an ionic liquid and sending a beam of electrons or applying a cold plasma at the surface of the solution in order to obtain the reduction of the salt of the metal. This process for the preparation of metal nanoparticles is specific to the ionic compounds of the invention, the cation of which is organic or organometallic, as they do not have a vapor pressure.

An ionic compound of the invention in which the cation is an organic or organometallic cation can also be used in the preparation of semiconductors, such as Si, Ge or their solid solutions, starting from their precursors (for example chlorides or bromides) dissolved in the liquid ionic compound.

Another subject matter of the invention is an electrolyte composition comprising an ionic compound and a solvent, characterized in that the ionic compound has a cation M of valency m ($1 \leq m \leq 3$) and m anions corresponding to the formula:

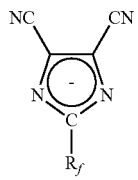

in which $R_f$ is a —CFZ'Z" group in which:
  Z' is F or a perfluoroalkyl group having from 1 to 3 carbon atoms,
  Z" is an H, F or Cl group, an optionally fluorinated or perfluorinated alkoxy group having from 1 to 5 carbon atoms, an optionally fluorinated or perfluorinated oxaalcoxy group having from 1 to 5 carbon atoms or an optionally fluorinated or perfluorinated alkyl group having from 1 to 5 carbon atoms,
  the cation being an inorganic cation, in particular an alkali metal cation, an alkaline earth metal cation or an ammonium cation, preferably a lithium ion or a sodium ion.

The solvent is chosen from liquid organic solvents optionally gelled by a polymer, solvating polymers optionally plasticized by a liquid solvent, mixtures of nonsolvating polymer and of a polar liquid or of an ionic liquid, and ionic liquids.

The term "liquid organic solvent" is understood to mean a polar liquid or a mixture of polar liquids capable of dissolving a salt of the present invention. Mention may in particular be made, as examples of polar liquids, of linear ethers and cyclic ethers, esters, nitriles, nitrated derivatives, amides, sulfones, sulfolanes, alkylsulfamides and partially halogenated hydrocarbons. The particularly preferred solvents are dimethoxyethane, glyme, tetrahydrofuran, dioxane, methyltetra-hydrofuran, methyl formate, ethyl formate, propylene carbonate, ethylene carbonate, alkyl carbonates (in particular dimethyl carbonate, diethyl carbonate and methyl propyl carbonate), butyrolactones, acetonitrile, benzonitrile, nitromethane, nitrobenzene, dimethylformamide, diethylformamide, N-methylpyrrolididone, dimethyl sulfone, tetramethylene sulfone, dimethyl sulfoxide and tetraalkylsulfonamides having from 5 to 10 carbon atoms, or their mixtures.

The term "ionic liquid" is understood to mean a salt or a mixture of salts of an inorganic or organic cation having a melting point $\leq 100°$ C. Mention may in particular be made, as examples of ionic liquids, of the salts of an organic cation and an anion chosen from the group consisting of $BF_4^-$, $CF_3SO_3^-$, TFSI, FSI, $C(CN)_3^-$ and $N(CN)_2^-$. Mention may in addition be made of the compounds of the present invention which have an organic or organometallic cation, in particular the salts of an ammonium, phosphonium, sulfonium, iodonium, pyridinium, imidazolium, pyrazolium, acetamidium, oxazolium, thiazolium, pyrrolidinium or piperidinium cation, more particularly the salts of a cation chosen from the (ethyl)(methyl)imidazolium, (butyl)(methyl)imidazolium, (methyl)(propyl)-pyrrolidinium, (methyl)(butyl)pyrrolidinium, (methyl)(propyl)piperidinium, butyl-pyridinium, (2-methoxyethyl)triethylammonium and hexyltrimethylammonium cations.

The term "solvating polymer" is understood to mean a polymer having a sufficient amount of the functional groups capable of forming a complex with the metal salts described above. Such a polymer can be chosen from crosslinked or noncrosslinked solvating polymers carrying or not carrying grafted ionic groups. Mention may be made, as example of solvating polymers, of polyethers with a structure which is linear, comb or block, forming or not forming a network, based on poly(ethylene oxide), or copolymers comprising the ethylene oxide or propylene oxide or allyl glycidyl ether unit, polyphosphazenes, crosslinked networks based on polyethylene glycol crosslinked by isocyanates or networks obtained by polycondensation and carrying groups which make possible the incorporation of crosslinkable groups. Mention may also be made of block copolymers in which some blocks carry functional groups which have redox properties.

The concentration of ionic compound in a liquid electrolyte composition according to the invention, in which the solvent is of the polar organic solvent type or of the ionic liquid type, is preferably between $10^{-3}$ mol/l and 3.5 mol/l.

In an electrolyte composition comprising a polymer solvent in which the polymer is composed of oxyalkylene repeat units, the concentration of ionic compound is preferably such that the number of oxygen atoms (or of repeat units) per mole of ionic compound is between 1 and 200.

Unexpectedly, the compounds of the invention have properties which are much better in terms of conductivity and of electrochemical stability than those of other conventional Hückel anions. In particular, the anions of the salts of the invention have an anodic stability of greater than 4.5 V vs. $Li^+/Li°$. This resistance to oxidation is entirely exceptional if it is considered that the anions of DCTA type and the anions of the salts of the invention are derived from $[ZO_2]^-$ acids by condensation with DAMN according to the following reaction scheme:

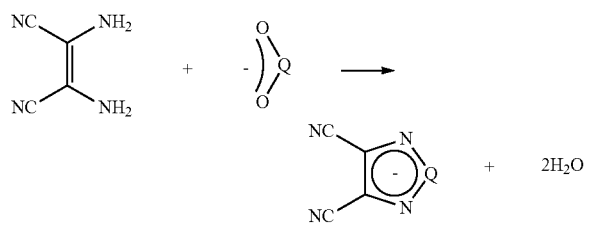

Q being N for the compounds of DCTA type of the prior art and $CR_f$ for the compounds of the present invention, in particular $CF_3C$.

It is thus possible to compare the acidities and oxidation potentials of DCTA and of the anions of the invention by comparing that of their acid precursor, that is to say nitrous acid $NO_2^-$, the $pK_a$ of which is 3.4, (for the compound of DCTA type) and trifluoroacetic acid $CF_3CO_2^-$, the $pK_a$ of which is 0.23 at 25° C., for the compound of the invention in which $R_f$ is $CF_3$. In the light of these values, it might have been supposed that the oxidation potential of the anion of the invention $R_f$=$CF_3$ would be shifted by 56×(3.4−0.23)=178 mV toward the anodic potentials, i.e. to ≈4V vs. $Li^+:Li°$. This potential would not be sufficient to provide for the electrochemical operation of the oxides of $Li_xT^MO_2$ (0≤x≤1) type or of the manganese phosphate $LiMnPO_4$ or of $LiMn_{1-y}Fe_yPO_4$ (0≤y<1). It is considered that an anodic stability of 4.3 V of the electrolyte is required for electrochemical generators using these cathode materials.

In point of fact, the voltammetric cycles carried out by various compounds of the invention in which $R_f$ is respectively —$CF_3$, —$CF_2Cl$, —$CF_2OCH_3$, —$CF_2OCF_3$, —$C_2F_5$, —$C_2F_4H$, —$C_3F_7$, or —$C_4F_9$ show that the oxidation potential of the compounds of the invention is greater than 4.3 V, far above that predicted by theory.

Just as surprisingly, the lithium salts of the compounds of the invention do not corrode aluminum at potentials below 4.6 V, which makes them excellent candidates for lithium batteries in which the current collector is an aluminum sheet, which has advantages of weight and cost.

An interesting advantage of several compounds of the invention is the low cost of the starting materials. For $R_f$=$CF_3$, trifluoroacetic acid is an industrial product which derives from the preparation of coolants (such as $CF_3CH_2F$, for example).

The electrolyte compositions of the present invention are of particular use in electrochemical devices which operate by exchange of lithium ions between an anode and a cathode. They are in particular lithium batteries, lithium-ion batteries, ultracapacitors and electrochromic devices. The ionic compound used is then preferably a lithium salt.

A compound (I) of the invention can be obtained by a process comprising:

a first stage consisting of preparing an acid

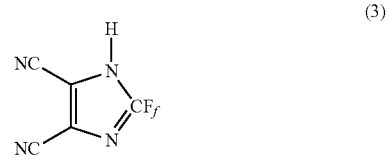

(3)

a second stage during which the acid is converted to the salt of the cation M.

The compound (3) can be obtained by reaction between DAMN and a reactant providing the $R_f$ group.

In a 1st embodiment, the first stage is carried out according to the following reaction scheme:

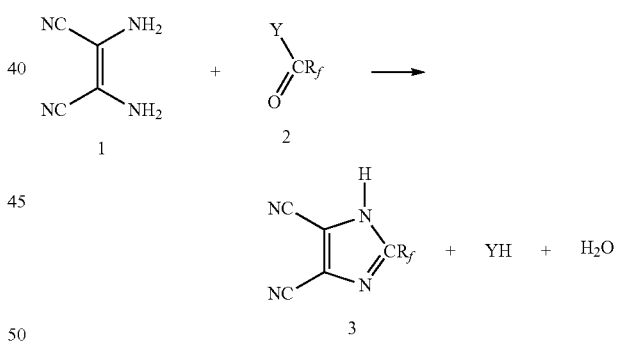

in which $R_f$ has the meaning given above and Y represents $R_fC(=O)O$, Cl, F, $CF_3SO_3$, $OCH_3$, $OC_2H_5$, $OCH_2CF_3$, $OC_6H_4NO_2$ (nitrophenyl), an imidazoyl group or a succinimidyloxy group.

In a 2nd embodiment, the first stage is carried out starting from an aldehyde (4) O=$CHR_f$, according to the following reaction scheme:

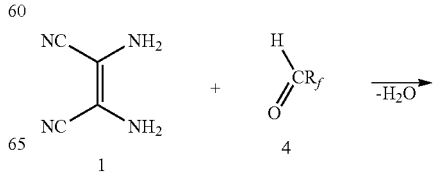

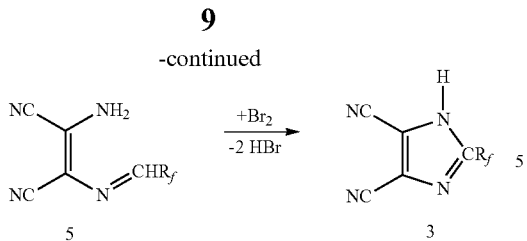

$R_f$ has the meaning given above.

In a 3rd embodiment, the 1st stage of the process is carried out starting from an acetal (6), according to the following reaction scheme:

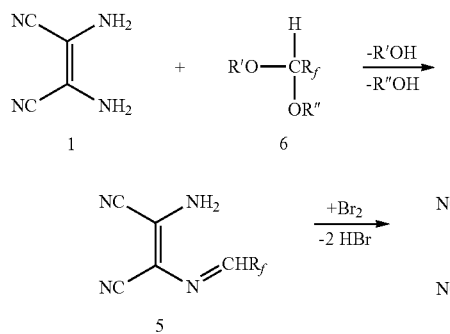

The 2nd and 3rd embodiments are advantageous when the aldehyde $R_fCHO$ or its acetals $R_fCH(OH)(OR')$, $R_fCH(OH)_2$, and $R_fCH(OR')(OR'')$ are commercially available, for example when R' and R'' are $CH_3$, $C_2H_5$, n-$C_3H_7$ or i-$C_3H_7$.

In the processes employing an aldehyde or an acetal, the bromine can be replaced by another oxidizing agent of similar strength for the cyclization of the compound (5). For example, bromine can be replaced by chlorine at low temperature or by an imide, such as N-chlorosuccinimide or N-bromosuccinimide, a hypochlorite or the sodium salt of N,N'-dichlorocyanuric acid.

The acid compound (3) obtained at the end of the 1st stage can be converted to the salt of the desired cation M by methods and techniques known to a person skilled in the art. Mention may be made in particular of the reaction of a compound (3) with a carbonate, a hydrogencarbonate, an acetate, a methyl carbonate or a hydroxide of the cation M. When the cation M is an organic cation, the conversion can be carried out in two stages: conversion of the acid compound (3) to the sodium or potassium salt and then reaction of the sodium or potassium salt with a stoichiometric amount of a compound of the organic cation (for example the chloride, the bromide or an alkyl sulfate) in an aprotic solvent in which the sodium or potassium salt is insoluble, for example acetonitrile.

A compound (2) in which the R' group of $R_f$ is F, and the R'' group and the Y group each represent an alkoxy or oxaalcoxy group $OZ^1$ (denoted by compound 2') can be obtained by reaction of a compound $HOZ^1$ (8) with tetrafluorooxirane (7), according to the reaction scheme:

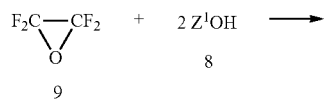

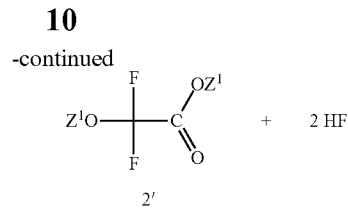

The compounds (2') concerned are in particular those in which $Z^1$ is an alkyl or an alkyloxyalkyl, said groups optionally being fluorinated or perfluorinated. Mention may be made, as example of group $OZ^1$, of the $OCH_3$, $OC_2H_5$, $OC_2H_4OCH_3$, $OC_2H_4OC_2H_5$, $OCH_2CF_3$ and $OCF_3$ groups.

A modification of the reaction in a basic medium makes it possible, starting from the anion $CF_3O^-$, to obtain derivatives of $CF_3OCF_2CO_2H''$. This alternative form makes it possible to prepare a compound in which the $R_f$ group is $CF_2OCF_3$.

A compound (2) in which the R' group of $R_f$ is $CF_3$ and the R'' group and the Y group each represent an alkoxy or oxaalcoxy group $OZ^2$ (denoted by compound 2'') can be obtained by reaction of a compound $HOZ^2$ (8) with the oxirane (10), according to the reaction scheme

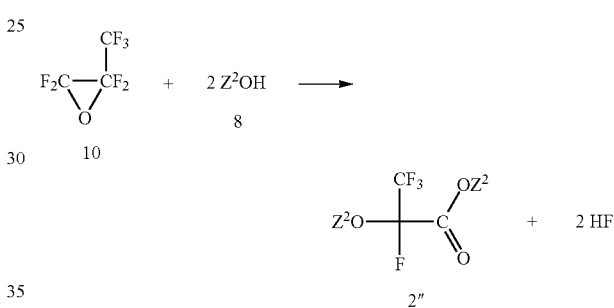

The compounds (2'') concerned are in particular those which comprise an $OZ^2$ group, such as $OCH_3$, $OC_2H_5$, $OC_2H_4OCH_3$, $OC_2H_4OC_2H_5$ or $OCH_2CF_3$.

The compounds $O=C(R_f)Y$ in which the $R_f$ group is $CF_3$, $CF_2H$, $CF_2Cl$, $C_2F_5$, $HC_2F_4$, $C_3F_7$ or $C_4F_9$ are available commercially in the form of acids, anhydrides or esters from which the formation of the ring of the dicyanoimidazole is possible.

The compounds (2) corresponding to the formula $O=C(R_f)Y$ can be prepared from the corresponding acid $O=C(R_f)OH$ by reaction with an appropriate reagent by processes known to a person skilled in the art. For example, the reagent is a chlorinating agent (for example $SOCl_2$) if Y is Cl, a carbonylimidazole if Y is an imidazole group, nitrophenyl carbonate if Y is a nitrophenyl group, or succinimidyl carbonate if Y is a succinimidyloxy group.

DETAILED DESCRIPTION

The present invention is illustrated by the following examples, to which it is not, however, limited.

Example 1

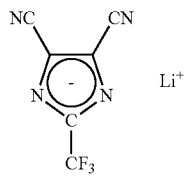

2.42 g of trifluoroacetic anhydride were introduced into a reactor comprising a solution of 1.14 g of DAMN in 11 ml of dioxane. The mixture was maintained under argon and stirred under reflux until the reactants had completely disappeared. After removing the solvent and the trifluoroacetic acid under vacuum, the solid residue was dissolved in 50 ml of ether. The ether solution was extracted 4 times with a suspension comprising 1 g of lithium carbonate in 90 ml of water and then the aqueous solution of the lithium salt was washed with ether. After removing the water in a rotary evaporator, the dark residue was dried under vacuum at 100° C. The dark-colored solid was subsequently extracted with acetonitrile (4×10 ml) and the resulting solution was filtered. The acetonitrile was subsequently removed and the crude salt was purified by chromatography on alumina using an acetonitrile/benzene 2/1 mixture as eluent. After drying, 1.45 g (yield 71%) of lithium 2-trifluoromethyl-4,5-dicyanoimidazole were obtained in the form of a colorless solid. The lithium salt (LiTDCI) is obtained in the form of a disolvate after recrystallization. The pure product is obtained by treatment under vacuum at 150° C.

Several samples of polymer electrolyte were prepared by dissolving 680 mg of poly(ethylene oxide), the molar mass $M_w$ of which is $10^5$, 200 mg of poly(ethylene oxide), the molar mass $M_w$ of which is $5 \times 10^6$, and LiTDCI in 13 ml of acetonitrile, with stirring, until a slightly opalescent and viscous solution is obtained.

Three samples were thus prepared using respectively 180 mg, 320 mg and 240 mg of LiTDCI.

Each of the solutions is run into a glass ring with a diameter of 50 cm positioned on a glass sheet covered with PTFE. After evaporating the acetonitrile under a stream of dry air, an elastic and transparent film of complex is obtained.

Figure 1:
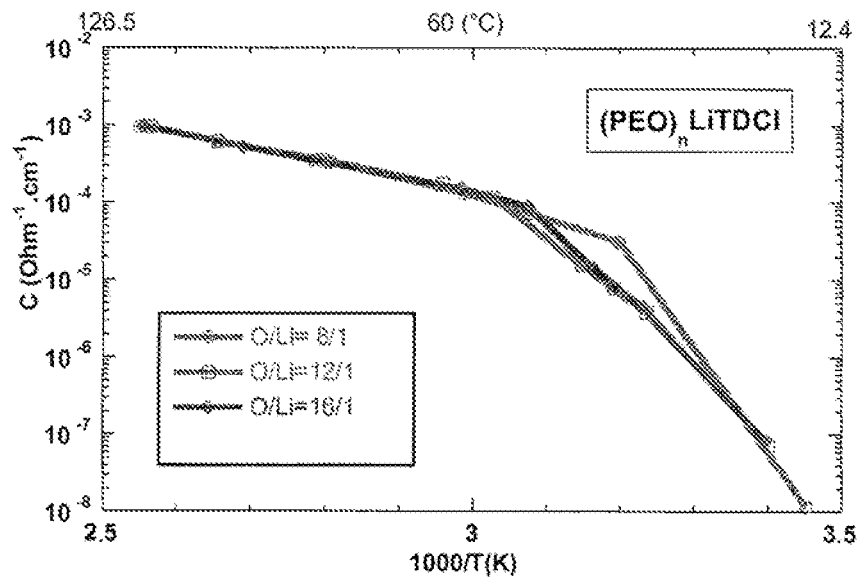
FIG. 1 is a graph of the conductivity C (in $ohm^- \cdot cm^{-1}$) as a function of the temperature, expressed in 1000/T(K), of example 1.

The conductivity of these electrolytes was measured as a function of the temperature. The conductivity C (in ohm$^{-1}$·cm$^{-1}$) as a function of the temperature, expressed in 1000/T(K), is represented in FIG. 1. The agreement between the curves and the samples is given in the table below:

| LiTDCI content | Sample | Curve |
| --- | --- | --- |
| 480 mg | P(EO)$_8$LiTDCI | O/Li = 8/1 |
| 320 mg | P(EO)$_{12}$LiTDCI | O/Li = 12/1 |
| 240 mg | P(EO)$_{16}$LiTDCI | O/Li = 16/1 |

The conductivity of LiTDCI is comparable to that of Li[CF$_3$SO$_2$)$_2$N] (LiTFSI), which is the reference salt for the conductivity of the polymer electrolytes.

Example 2

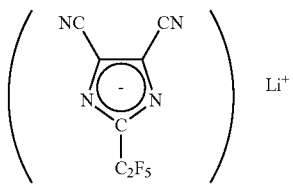

10.5 ml (53.8 mmol) of pentafluoropropionic anhydride were added to a solution of 4.84 g (44.8 mmol) of diaminomaleonitrile in 47 ml of dioxane. The mixture was heated at reflux under argon until the precipitate had disappeared [confirmed by thin layer chromatography (TLC), approximately 6 h]. The resulting mixture was placed under vacuum at 90° C. for 1 h and then dried on a high vacuum line at 120° C. for 1 h in order to remove the solvent and the acid. The solid residue was dissolved in 40 ml of ether and the resulting solution was extracted three times with a suspension of 3 g (40.5 mmol) of lithium carbonate in 100 ml of water. The aqueous salt solution was washed twice with 50 ml of ether. Subsequently, active charcoal, acting as decolorant, was added to the aqueous solution and the slurry was heated for 1 h. After removing the active charcoal by filtration through a filter paper, the solution was dried under vacuum at 80° C. for 2 h. Subsequently, the residue was dissolved in anhydrous acetonitrile and the solid residue was again filtered off. The acetonitrile solution was placed under vacuum at 90° C. for 1 h. A double crystallization from an acetonitrile/benzene 1/1 mixture gave crystals which were placed under vacuum on a high vacuum line at 120° C. for 4 h. 5.12 g of colorless crystals of lithium 4,5-dicyano-2-(pentafluoroethyl)imidazole [LiPDCI] were obtained (yield: 47.2%).

Example 3

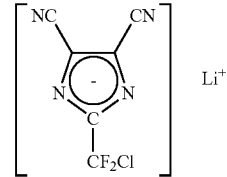

10.8 g of DAMN and 22 g of chlorodifluoroacetic anhydride (ClF$_2$CO)$_2$O are added to 100 ml of diglyme and brought to reflux under a protective nitrogen atmosphere, and the reaction is continued for 48 hours. The reaction products are filtered and treated with 12 g of sodium carbonate, and the solution is evaporated. The solid residue is taken up in 80 ml of water and 25 g of sulfamic acid. The mixture of 2-chlorodifluoroethyl-4,5-dicyanoimidazole and of the reaction byproduct chlorodifluoroacetic acid is extracted with three portions of 50 ml of ether. The portions are combined and evaporated. The crude 2-chlorodifluoro-methyl-4,5-dicyanoimidazole is purified by sublimation under low vacuum at 90° C. in a Büchi oven.

The lithium salt is obtained by reacting 5 g of the acid form of the imidazole with a slight stoichiometric excess of lithium carbonate (1.1 g) in acetonitrile. The suspension is centrifuged and the lithium salt Li[CClF$_2$C$_3$N$_2$(CN)$_2$] is obtained in the form of a hygroscopic white powder.

Example 4

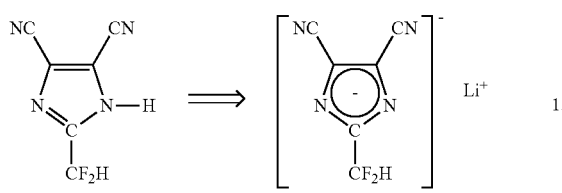

16.2 g of commercial carbonyldiimidazole are added to 9.6 g of commercial difluoroacetic acid in 75 ml of diglyme. Evolution of CO$_2$ occurs after a few minutes. 10.8 g of DAMN are added to the clear solution obtained. The reaction is maintained at reflux under a nitrogen atmosphere for 24 hours. The diglyme is evaporated under reduced pressure and 100 ml of 2M HCl are added. The 2-difluoromethyl-4,5-dicyanoimidazole is extracted with three portions of ether of 30 ml. After evaporating the combined extracts, the product is purified by sublimation under vacuum at 115° C. under low vacuum. The lithium salt is, as in the preceding examples, obtained from lithium carbonate in slight excess in acetonitrile.

Example 5

The methyl ester of 3,3,3-trifluoromethoxy-2-fluoro-2-methoxypropanoic acid was prepared by condensation of 16 g of epoxyhexafluoropropene C$_3$F$_6$O in 75 ml of anhydrous methanol at −30° C. The ester is separated by diluting with water, extracting with dichloromethane and distilling. 8.5 g of CF$_3$C(OCH$_3$)FC(=O)OCH$_3$ are hydrolyzed with 2.4 g of sodium hydroxide in ethanol, the solvent is evaporated and the solid is taken up in acetonitrile, in which only CF$_3$C (OCH$_3$)FCO$_2$Na is soluble. Said salt is subsequently separated by filtration and evaporation of the ethanol.

9.9 g of said sodium salt and 4.95 g triphosgene (CCl$_3$O)$_2$C=O are reacted in the presence of 50 mg of dimethylformamide (DMF) as catalyst in dioxane at 0° C. 5.40 g of DAMN are added and the mixture is brought to reflux under a nitrogen atmosphere for 24 hours. The imidazole A5 is converted to the lithium salt B5 by the action of lithium carbonate.

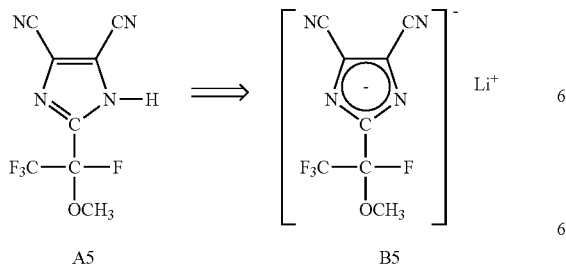

Example 6

An ionic liquid is prepared by the action of 3.84 g of the lithium salt of example 1 on 4.75 g of (ethyl)(methyl)imidazolium ethyl sulfate N$_2$O$_4$SC$_8$H$_{16}$ in 30 ml of water. The ionic liquid which separates is extracted with dichloromethane and washed three times with water. After evaporating the solvent, a fluid oil is obtained which corresponds to the formula:

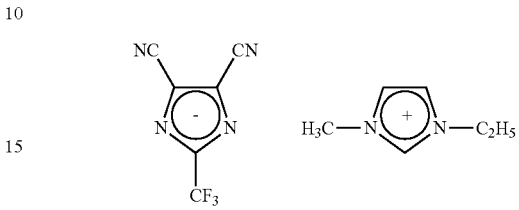

This fluid does not have a detectable vapor pressure and is stable at up to 375° C.

Example 7

The 2-methoxyethyl ester of difluoro(2-methoxyethoxy) acetic acid is obtained by condensation of 16.6 g of epoxytetrafluoroethylene C$_2$F$_4$O in 250 ml of anhydrous methoxyethanol at −30° C.

The ester CH$_3$O—C$_2$H$_4$O—F$_2$C—C(=O)—OCH$_2$CH$_2$OCH$_3$ is separated by distillation. 11.4 g of ester are hydrolyzed with 3 g of potassium hydroxide in ethanol, the solvent and the resulting methoxyethanol are evaporated and then the solid is dried under vacuum at 70° C. The solid is taken up in acetonitrile, in which only the potassium salt CH$_3$O—C$_2$H$_4$O—CF$_2$—CO$_2$K is soluble. This salt is recovered by filtration and evaporation.

6.6 g of potassium salt, 4 g of thionyl chloride SOCl$_2$ and 50 mg of dimethylformamide (DMF), as catalyst, are reacted in 35 ml of diglyme at 0° C. After 1 h, 3.6 g of DAMN are added and the mixture is brought to reflux under a nitrogen atmosphere for 24 hours. The imidazole A7, extracted and purified as in example 5, is converted to the lithium salt B7 by the action of lithium carbonate.

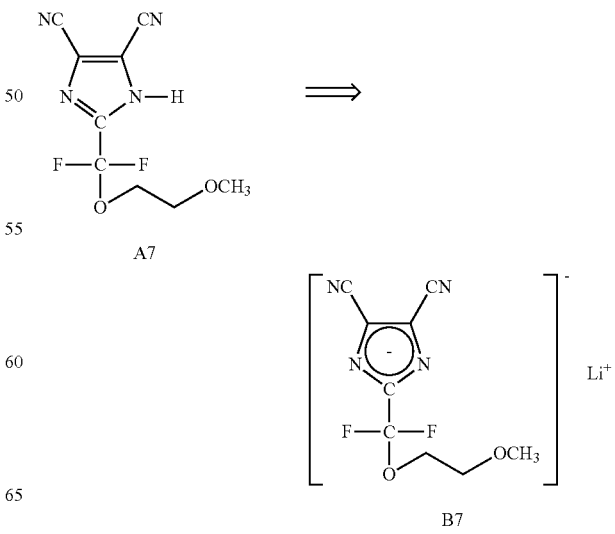

Example 8

Butylpyridinium bromide is prepared by a Menshutkin reaction of 27.5 g of 1-bromobutane with 15.8 g of pyridine at 40° C. in 24 hours, without solvent. The solid obtained is dried under low vacuum at 50° C.

An ionic liquid is prepared by the action of 4.84 g of the lithium salt of example 2 $(CN)_2C_3N_2C_2F_5Li$ on 4.35 g of butylpyridinium bromide in 25 ml of water. The ionic liquid which separates is extracted with dichloromethane and washed three times with water. After evaporating the solvent, a fluid oil is obtained which corresponds to the formula:

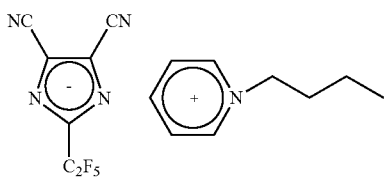

This fluid does not have a detectable vapor pressure and is stable at up to 375° C.

Example 9

(Propyl)(methyl)pyrrolidinium bromide is prepared by reaction of 12.4 g of 1-bromopropane with 8.5 g of N-methylpyrrolidine at normal temperature.

An ionic liquid is prepared by the action of 3.84 g of the salt $(CN)_2C_3N_2CF_3Li$ obtained according to example 1 on 4.18 g of (propyl)(methyl)pyrrolidinium bromide in 25 ml of water. The ionic liquid which separates is extracted with dichloromethane and washed three times with water. After evaporating the solvent, a fluid oil is obtained which corresponds to the formula:

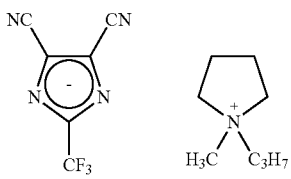

This fluid does not have a detectable vapor pressure and is stable at up to 375° C.

Example 10

18 g of commercial pentafluoropropionaldehyde hemiacetal $C_2F_5CH(OH)OCH_3$ are added to 10.8 g of DAMN in 50 ml of acetonitrile. The mixture is maintained at 50° C. with stirring for 24 hours. Subsequently, the reaction mixture is cooled to −10° C. and 16 g of bromide in acetonitrile are added dropwise. The solvent is evaporated. The crude 2-pentafluoroethyl-4,5-dicyanoimidazole is purified by sublimation at 100° C. under vacuum in a Büchi oven. The lithium salt is prepared as above by the action of lithium carbonate.

Example 11

The conductivity of the lithium salt LiTDCI of example 1 and of the salt LiPDCI of example 2 was compared with that of various salts of the prior art known for lithium batteries. The measurements were carried out starting from a 1M solution of each salt in an ethylene carbonate/methyl carbonate (EC/DMC) 50/50 v/v mixture, at 20° C.

| Salt | Conductivity (mS · cm$^{-1}$) |
| --- | --- |
| LiPF$_6$ | 10.8 |
| LiTFSI | 9.0 |
| LiTDCI | 6.7 |
| LiPDCI | 6.3 |
| LiDCTA | 2.9 |

This table shows that the performances of LiTDCI and LiPDCI are markedly better than those of LiDCTA, the conductivity being more than doubled.

Example 12

Three batteries of the "Swagelok" type:
Li/1M salt in EC-DMC electrolyte/LiFePO$_4$
comprising a lithium anode, a liquid electrolyte composed of a 1M solution of a salt in an EC/DMC 50/50 mixture, and a cathode composed of a mixture of LiFePO$_4$ comprising 15% by weight of carbon SP on a Pt collector, were assembled.

The salt is respectively the salt LiTDCI of example 1, the salt LiPDCI of example 2 and, by way of comparison, the salt LiPF$_6$.

Figure 2:
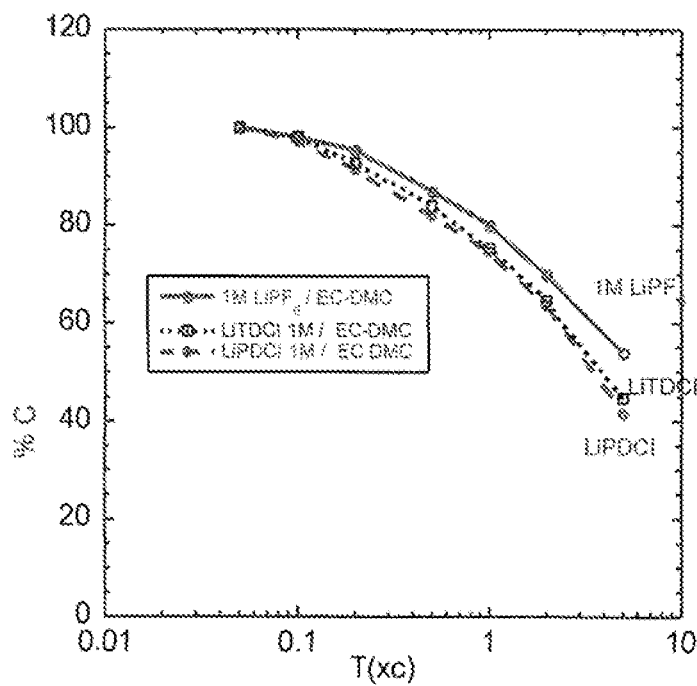
FIG. 2 shows Ragone curves, in which "% C" on the ordinate indicates the percentage of capacitance remaining, as a function of the rate of discharge t(xc), indicated on the abscissa and T(xc) represents the inverse of the time, in hours, with respect to Example 12.

The ability to retain its capacitance as a function of the power demanded was confirmed for each of the batteries according to the following process. Each battery was operated several times, with a different applied current, at 22° C., and the time necessary in order to obtain complete discharge as a function of the theoretical time necessary for a complete discharge was recorded. The results are represented by the Ragone curves of FIG. 2, in which "% C" on the ordinate indicates the percentage of capacitance remaining, as a function of the rate of discharge t(xc), indicated on the abscissa. T(xc) represents the inverse of the time, in hours.

These curves show that the batteries in which the salt of the electrolyte is a compound according to the invention have a comparable performance to that of a battery in which the electrolyte is LiPF$_6$, regarded as one of the most conductive salts currently used in liquid electrolyte lithium batteries.

Example 13

Batteries analogous to those of example 12 were assembled using an aluminum current collector for the cathode for the purpose of testing the resistance to corrosion of the aluminum as a function of various electrolyte compositions.

The salt is respectively the LiTDCI salt of example 1, the LiPDCI salt of example 2 and, by way of comparison, the salt LiPF$_6$ and the salt LiTFSI.

Each battery was subjected to cyclic voltammetry with conditions of 10 mV/min.

Figure 3:
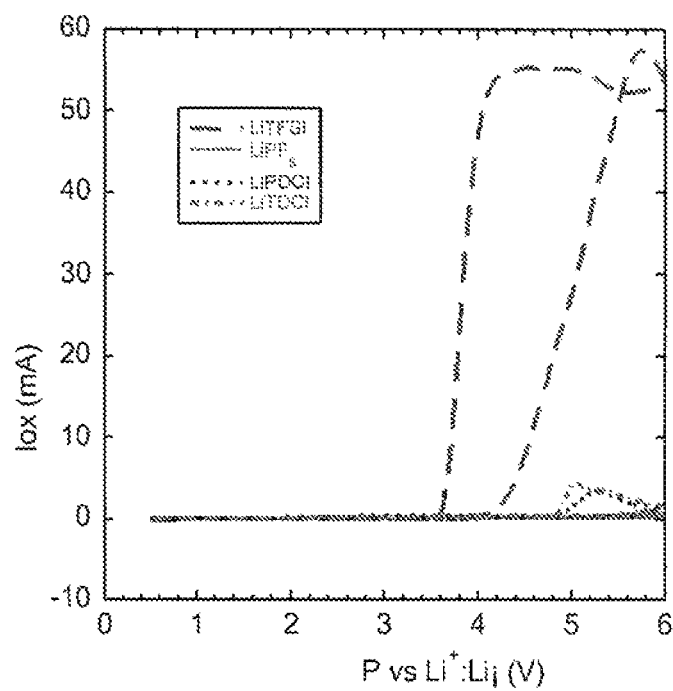
FIG. 3 is a graph showing the results from example 13, in which the oxidation current $I_{ox}$ in mA is given on the ordinate, as a function of P (potential vs. $Li^+/Li$) in volts.

The results are given in FIG. 3, in which the oxidation current $I_{ox}$ in mA is given on the ordinate, as a function of P (potential vs. Li$^+$/Li) in volts.

As expected, LiPF$_6$ does not give appreciable corrosion and LiTFSI, on the other hand, proves to be highly corrosive. The salts of the invention, LiTDCI and LiPDCI, do not give corrosion before their oxidation at 4.6 V vs. Li$^+$:Li°. It should be remembered that the majority of electrode materials of oxide or Li$_{1-x}$Fe$_x$PO$_4$ type finish their recharging at 4.3 V vs. Li$^+$:Li°, which shows the advantage of the compounds of the invention, which do not corrode the aluminum at this potential.

Example 14

Three batteries of the "button cell" type Li/salt+POE electrolyte/LiFePO$_4$ comprising a lithium anode, a polymer electrolyte composed of a solid solution of a salt in a poly(oxyethylene) POE, and a positive electrode composed of a mixture of 40% of LiFePO$_4$, 10% of carbon SP and 50% of PEO as fraction by weight on a collector made of stainless steel, were assembled.

Each of the electrolytes is prepared according to the procedure of example 1, to form films with a thickness of ≈100 μm, using amounts of polymer and of lithium salt in order to obtain a ratio O/Li=20.

The salt is respectively the salt LiTDCI of example 1, the salt LiPDCI of example 2 and, by way of comparison, the salt LiTFSI.

Figure 4:
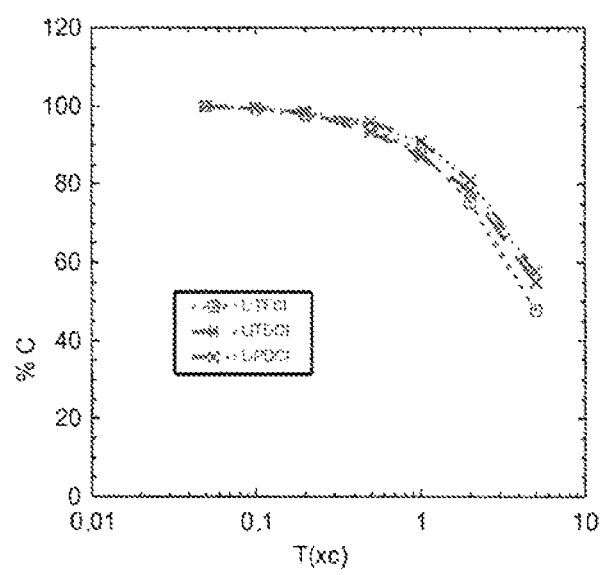
FIG. 4 shows Ragone curves, in which "% C" on the ordinate indicates the percentage of capacitance remaining, as a function of the rate of discharge t(xc), indicated on the abscissa. T(xc) represents the inverse of the time, in hours, with respect to example 14.

The ability to retain its capacitance as a function of the power demanded was confirmed for each of the batteries according to the following process. Each battery was operated several times, with a different applied current, at 80° C., and the time necessary in order to obtain complete discharge as a function of the theoretical time necessary for a complete discharge was recorded. The results are represented by the Ragone curves of FIG. 4, in which "% C" on the ordinate indicates the percentage of capacitance remaining, as a function of the rate of discharge t(xc), indicated on the abscissa. T(xc) represents the inverse of the time, in hours.

These curves show that the batteries in which the salt of the electrolyte is a compound according to the invention have a comparable performance to that of a battery in which the electrolyte is LiTFSI, regarded as one of the most conductive salts currently used in polymer electrolyte lithium batteries.

What is claimed is:

1. An electrolyte composition composed of a salt in solution in a solvent, characterized in that the salt is a compound comprising an inorganic cation M of valency m, where 1≤m≤3, chosen from alkali metal cations, alkaline earth metal cations and the ammonium ion, and m anions corresponding to the formula:

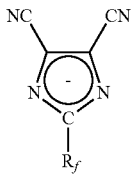

in which R$_f$ is a —CFZ'Z" group in which:
   Z' is F or a perfluoroalkyl group having from 1 to 3 carbon atoms,
   Z" is an H, F or Cl group, an alkoxy group having from 1 to 5 carbon atoms, an oxaalcoxy group having from 1 to 5 carbon atoms or an alkyl group having from 1 to 5 carbon atoms.

2. The electrolyte composition as claimed in claim 1, wherein R$_f$ is chosen from the group consisting of CF$_3$, CF$_2$H, CF$_2$Cl, C$_2$F$_5$, CF$_2$CF$_2$H, C$_3$F$_7$, C$_4$F$_9$, CF$_2$OCH$_3$, CF$_2$OC$_2$H$_5$, CF$_2$OC$_2$H$_4$OCH$_3$, CF$_2$OC$_2$H$_4$OC$_2$H$_5$, CF$_2$OCH$_2$CF$_3$, CF(CF$_3$)OCH$_3$, CF(CF$_3$)OC$_2$H$_5$, CF(CF$_3$)OC$_2$H$_4$OCH$_3$ and CF(CF$_3$)OC$_2$H$_4$OC$_2$H$_5$.

3. The electrolyte composition as claimed in claim 1, wherein the cation of the salt of the electrolyte is either one of a lithium ion or a sodium ion.

4. The electrolyte composition as claimed in claim 1, wherein the solvent is selected from the group consisting of liquid organic solvents, solvating polymers, and ionic liquids.

5. The electrolyte composition as claimed in claim 4, wherein the ionic liquid is a compound comprising a cation M of valency m (1≤m≤3) and m anions corresponding to the formula:

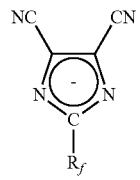

in which R$_f$ is a —CFZ'Z" group in which:
   Z' is F or a perfluoroalkyl group having from 1 to 3 carbon atoms,
   Z" is an H, F or Cl group, an alkoxy group having from 1 to 5 carbon atoms, an oxaalcoxy group having from 1 to 5 carbon atoms or an alkyl group having from 1 to 5 carbon atoms;
the cation being an organic cation chosen from ammonium, phosphonium, sulfonium, iodonium, pyridinium, imidazolium, pyrazolium, acetamidium, oxazolium, thiazolium, pyrrolidinium and piperidinium ions.

6. The electrolyte composition as claimed in claim 5, wherein the cation of the compound forming the ionic liquid is selected from the group consisting of (ethyl)(methyl)imidazolium, (butyl)(methyl)imidazolium, (methyl)(propyl)pyrrolidinium, (methyl)(butyl)pyrrolidinium, (methyl)(propyl)piperidinium, butylpyridinium, (2-methoxyethyl)triethylammonium and hexyltrimethylammonium cations.

7. The electrolyte composition as claimed in claim 4, wherein the solvent is a polar liquid or a mixture of polar liquids and the concentration of salt is from $10^{-3}$ mol/l to 3.5 mol/l.

8. The electrolyte composition as claimed in claim 4, wherein the solvent is a solvating polymer comprising oxyalkylene repeat units and the concentration of salt is such that the number of oxygen atoms (or repeat units) per mole of salt is between 1 and 200.

9. The electrolyte composition as claimed in claim 4, wherein the solvent is an ionic liquid and the concentration of salt is from $10^{-3}$ mol/l to 3.5 mol/l.

* * * * *